United States Patent [19]
Sorenson et al.

[11] Patent Number: 5,368,017
[45] Date of Patent: Nov. 29, 1994

[54] APPARATUS FOR VENTILATING AND ASPIRATING

[75] Inventors: James L. Sorenson, Salt Lake City; Valdon G. Reynolds, Bountiful; Stephen C. Mackert; Joseph H. Jeffs, both of Sandy; David W. Kaufman, Salt Lake City, all of Utah

[73] Assignee: Sorenson Laboratories, Inc., Salt Lake City, Utah

[21] Appl. No.: 848,030

[22] Filed: Mar. 9, 1992

Related U.S. Application Data

[63] Continuation-in-part of Ser. No. 678,663, Apr. 1, 1991, Pat. No. 5,325,851.

[51] Int. Cl.[5] .............................................. A61M 16/00
[52] U.S. Cl. ........................... 128/200.26; 128/207.14; 128/207.16; 128/912
[58] Field of Search .................. 128/200.26, 207.14, 128/207.15, 207.16, 912, DIG. 26; 604/171, 159, 160, 163; 383/64, 63, 100

[56] References Cited

U.S. PATENT DOCUMENTS

| | | | |
|---|---|---|---|
| 3,185,152 | 5/1965 | Ring | 604/159 |
| 3,262,448 | 7/1966 | Ring et al. | 604/159 |
| 3,788,305 | 1/1974 | Schreiber | 604/159 |
| 4,834,726 | 5/1989 | Lambert | 604/281 |
| 4,838,255 | 6/1989 | Lambert | 128/207.16 |
| 5,029,580 | 7/1991 | Radford et al. | 128/207.14 |
| 5,083,561 | 1/1992 | Russo | 128/207.16 |
| 5,125,893 | 6/1992 | Dryden | 604/171 |
| 5,171,222 | 12/1992 | Euteneuer et al. | 604/160 |

FOREIGN PATENT DOCUMENTS 904237  8/1962  United Kingdom ............... 604/160

Primary Examiner—Edgar S. Burr
Assistant Examiner—Aaron J. Lewis
Attorney, Agent, or Firm—Trask, Britt & Rossa

[57] ABSTRACT

A ventilating and aspirating apparatus for delivering respiratory gases to the trachea and the congested lungs and breathing passageways of a patient includes a flexible catheter tube extendable into and withdrawable from the patient's trachea. The catheter is housed within a pliable sheath extending from a manifold that is attachable to an endotracheal tube. The sheath has a slit defined by backing members formed along elongate opposed edges. A releasable, air tight "ziplock" seal is effected at the slit by a bead on one backing member and a groove to sealingly receive the bead on the other backing member. A "ziplock" actuator is structured as a slider member which travels along the bead and groove, and includes converging ends to hold the bead in the groove and a conduit member extending centrally through the slider member to interconnect an end of the catheter tube inside the sheath through a vacuum valve carried by the slider member outside the sheath to a vacuum source. The vacuum valve is operable by the same hand of a user that may be used to move the slider member.

70 Claims, 7 Drawing Sheets

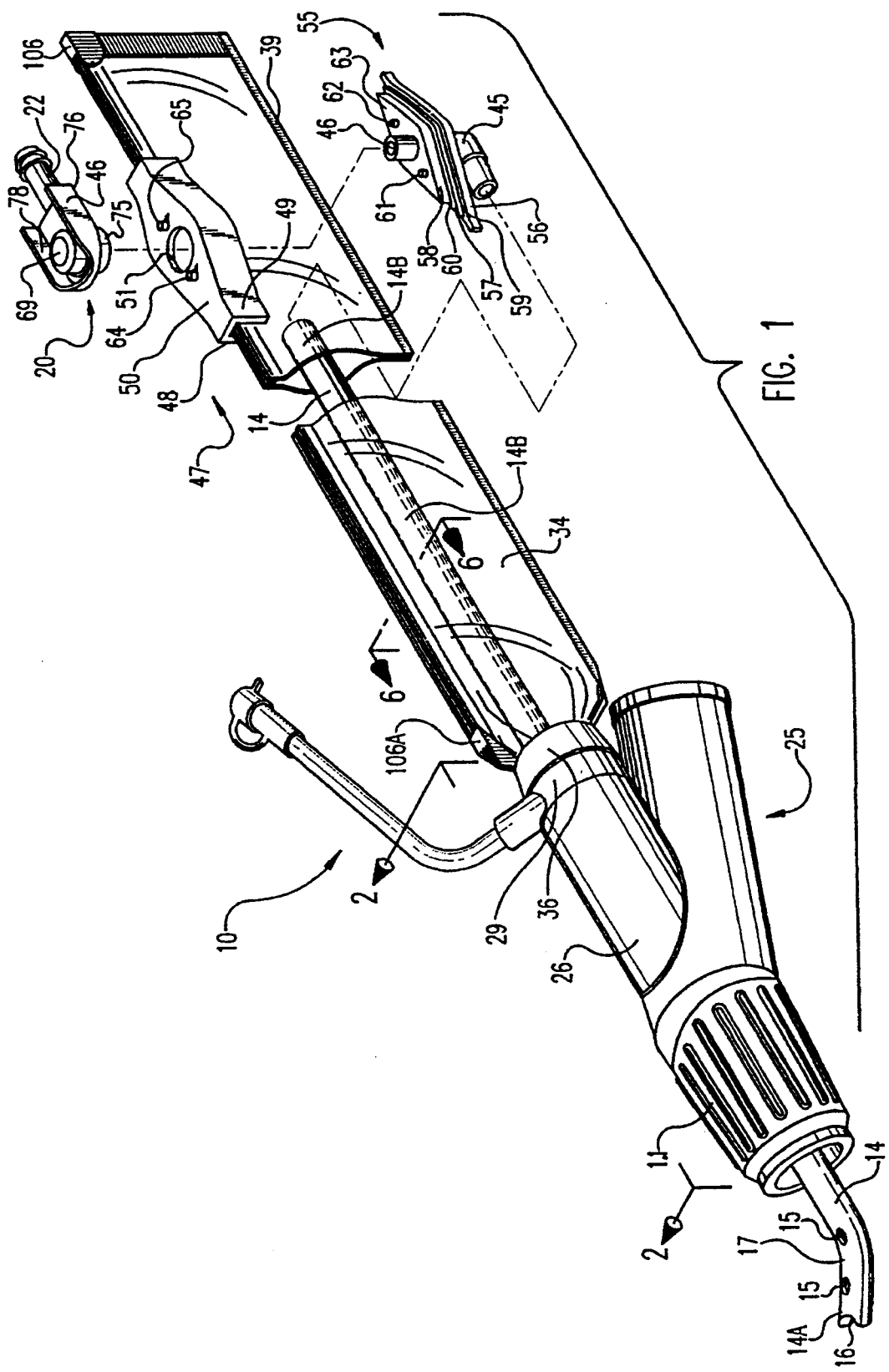

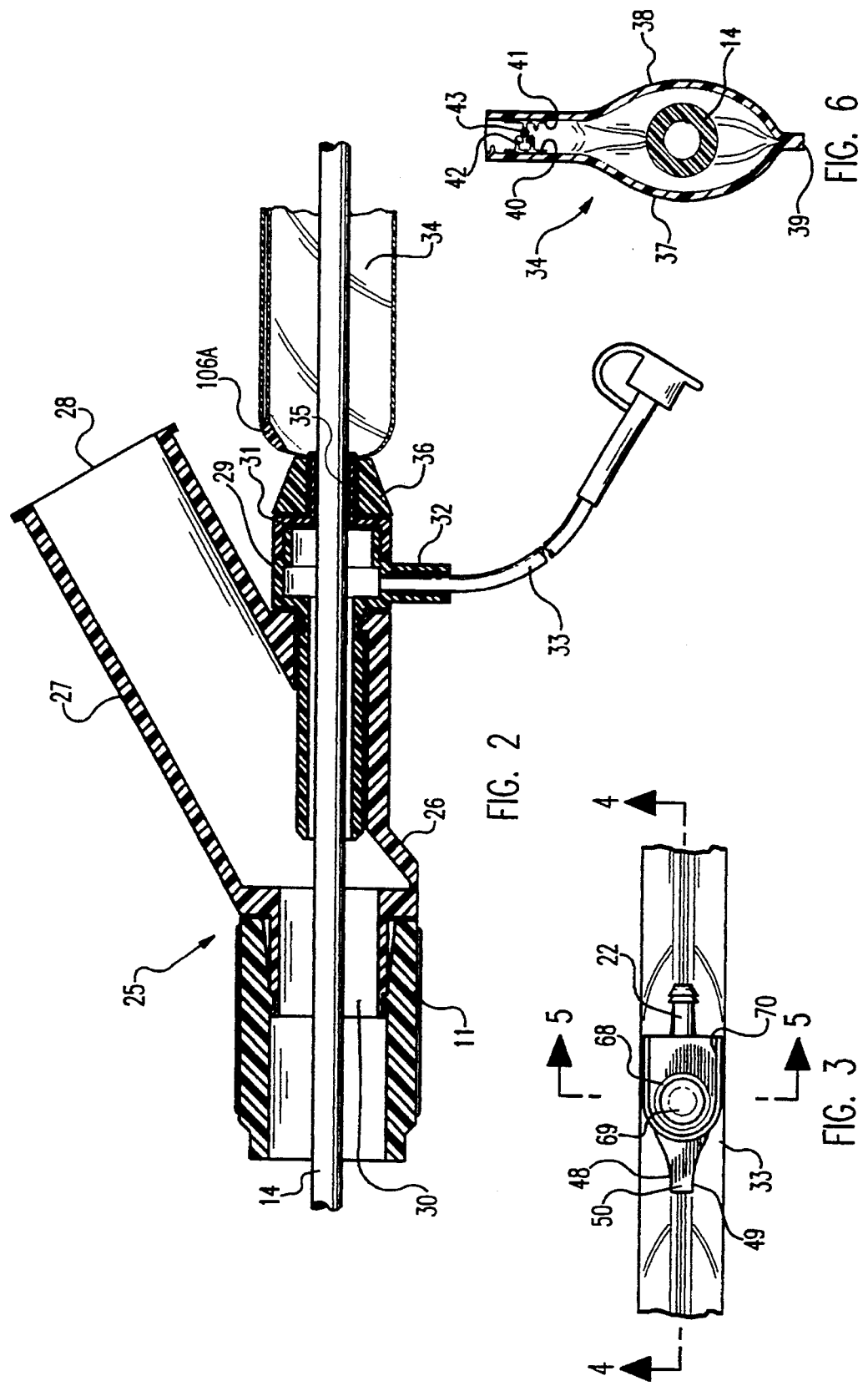

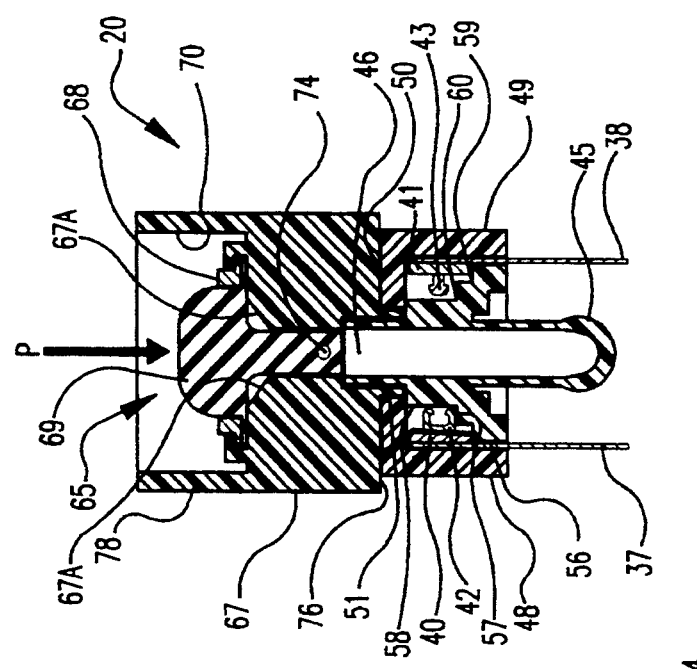
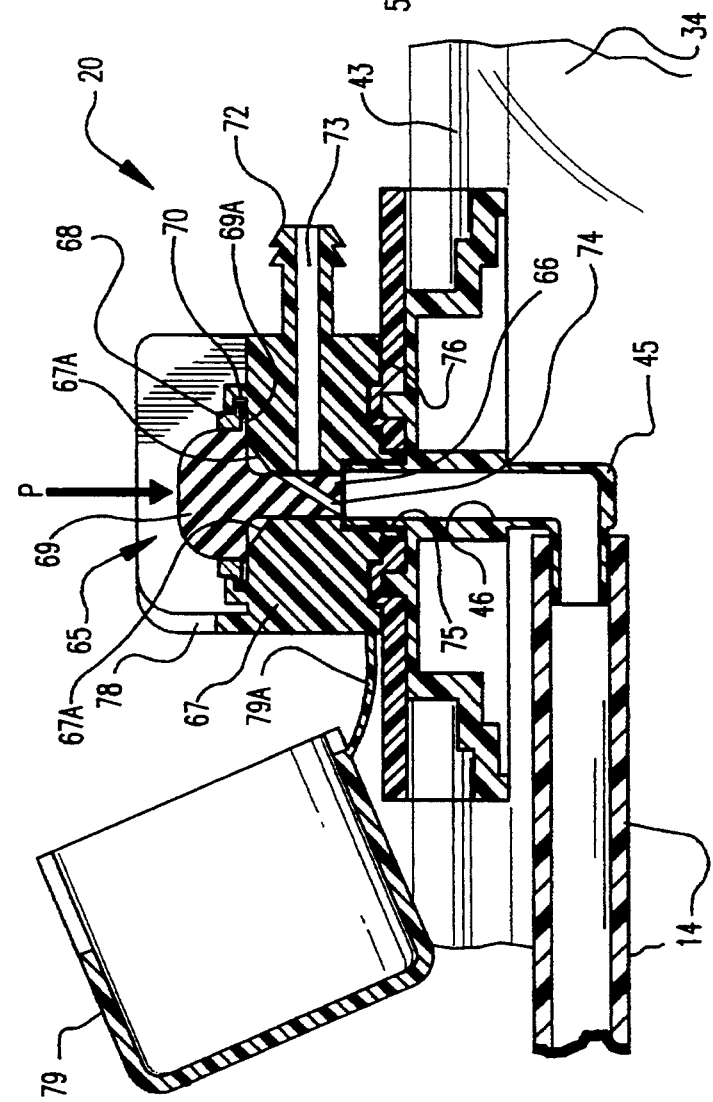

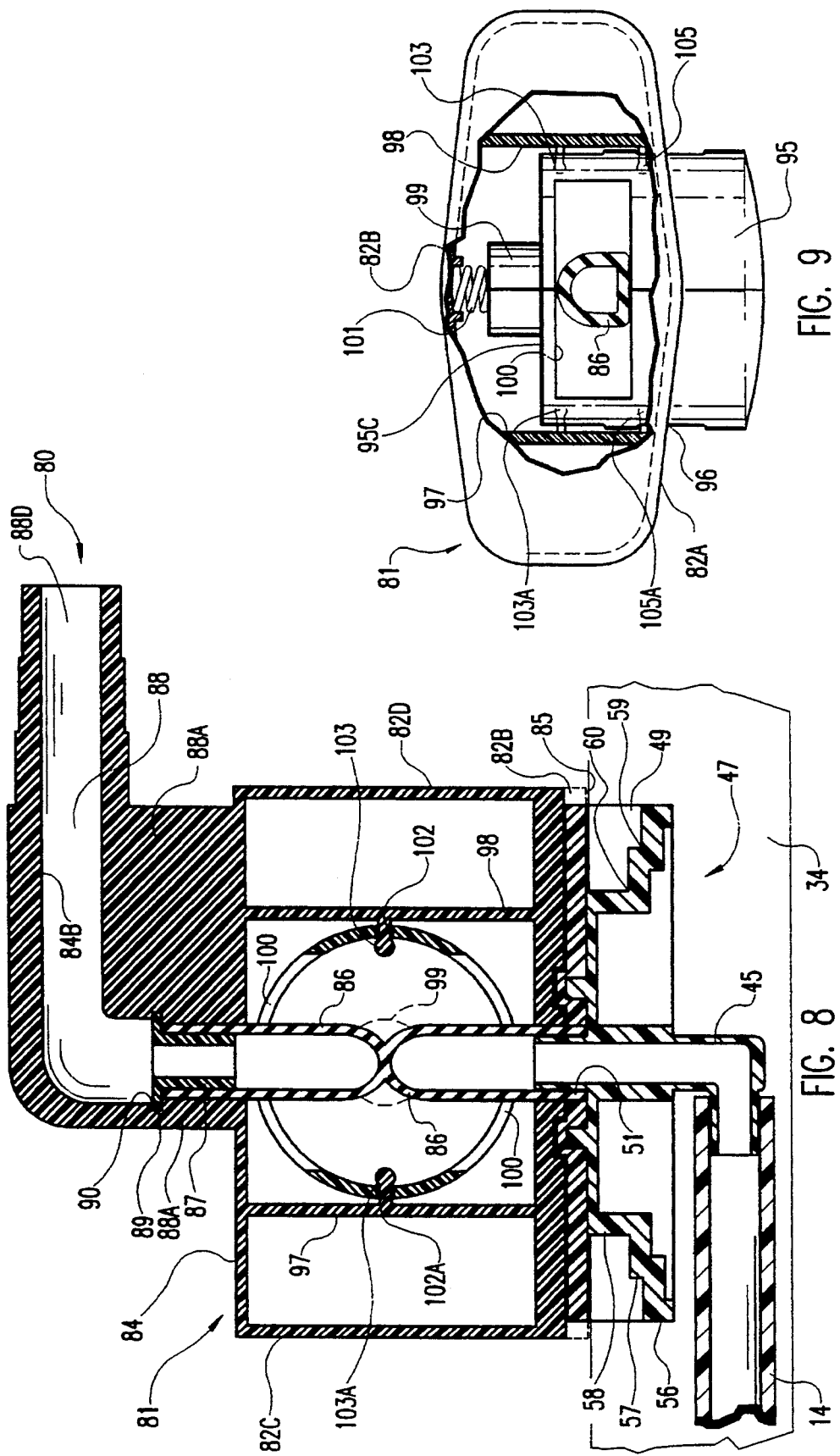

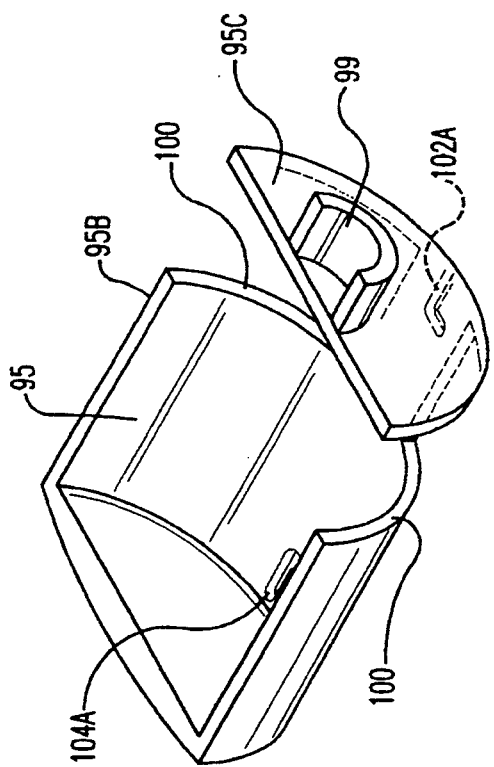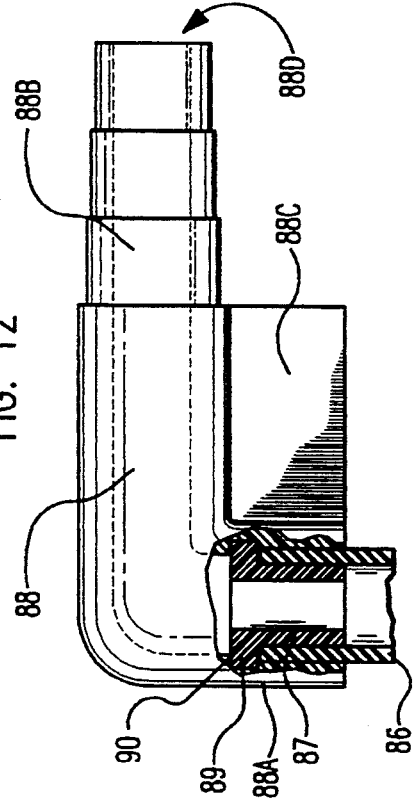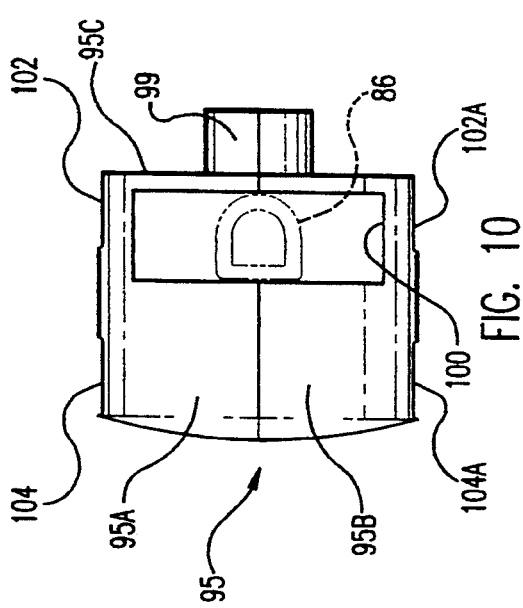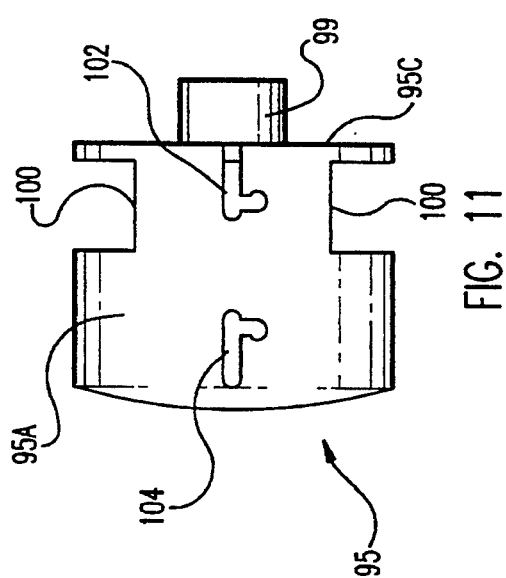

APPARATUS FOR VENTILATING AND ASPIRATING

BACKGROUND OF THE INVENTION

RELATED APPLICATIONS

This application is a continuation in part of commonly assigned, copending application Ser. No. 678,663, filed Apr. 1, 1991, now U.S. Pat. No. 5,325,851. The parent application discloses an apparatus and method for ventilating and aspirating the lungs of a medical patient. The present application discloses and claims improved versions of the apparatus which are useful in the same general context as disclosed in the parent application.

FIELD

This invention relates generally to an apparatus for ventilating and aspirating the lungs of a medical patient and is particularly directed to an improved apparatus for ventilating and aspirating congested lungs and obstructed breathing passageways.

STATE OF THE ART

Apparatus for the ventilating and aspirating of lungs of a medical patient have been proposed in the past. U.S. Pat. Nos. 4,836,199; 4,569,344; and 3,991,762 each disclose a device in which a flexible catheter tube is sealed inside a collapsible plastic envelope. This arrangement is intended to assure sterility even when the catheter tube is removed from the trachea of a patient. The catheter of the device is attached at its proximal (user) end to a valve so that a vacuum source can be selectively communicated to the catheter lumen. The device also contains a manifold which attaches to an endotracheal tube and a ventilating fixture. Insertion of the catheter tube into the trachea of the patient is accomplished by grasping the catheter tube through the envelope and manually moving it into the trachea. Each of the patented devices also contains a port through which the exterior of the catheter tube can be rinsed with a suitable irrigating solution. The '762 patent further discloses a wheel attached to the catheter tube so that it can be rotated during its insertion or removal.

As is noted in the parent application, the ventilating/aspirating devices of the above-identified patents are not always entirely satisfactory. The catheter tubes are relatively pliant and lack any structural reinforcement. Consequently, such a device tends to fall where it may, interfering with both patient movement and patient care. Further, the device itself tends to interfere with other structures attached to the patient. Structures such as intravenous delivery tubing or electronic sensors may become tangled with the pliant catheter tube. Moreover, the catheter tube cannot conveniently be taped to the patient or secured out of the way because it must be positioned generally in line with the endotracheal tube to facilitate insertion of the catheter into the patient.

These prior art devices also require a user to employ both hands when inserting the catheter into the trachea of a patient. One hand must grasp the catheter tube to insert it incrementally into the trachea, while the other hand must hold either the manifold body (to ease insertion) or the proximal end of the device (to keep it out of the way). If aspiration is desired during the insertion step, a second person must operate the valve.

Indiscriminate movement of the pliant catheter tube, repeated insertion into the patient, or exposure to objects which can penetrate the flexible envelope result in inadequate assurance of sterility. Pinholes in the envelope can easily occur, exposing the catheter to outside air and thereby compromising sterility of the catheter. Similarly, pinholes can expose users to contaminants from the patient.

In the aforementioned parent application Ser. No. 678,663, the disclosure of which is incorporated by reference as a part of this disclosure, there is disclosed an improved apparatus for simultaneously ventilating and aspirating a medical patient. The apparatus disclosed enables a user to insert a flexible catheter tube into either lung of a patient in one smooth motion without risk of contamination or infection. Additionally, a user is able to activate, in one motion, a vacuum valve to evacuate undesired respiratory fluids and simultaneously ventilate and/or irrigate the lungs. A flexible catheter tube is attached at the proximal (user) end to a valve that is operable to communicate a suctioning vacuum to the lumen of the catheter. The valve is normally closed and is biased to the closed position by a resilient cap carrying a depending valve stem. When the resilient cap is depressed by a user, a passage through the valve stem communicates flow between the catheter tube and a connector nipple to which the suction source is connected. When the user releases the cap, the natural resiliency of the cap moves the passage in the stem out of registration and flow through the valve is stopped.

The catheter tube disclosed by the parent application slides within a semi-rigid sheath and through a manifold that may be connected to an endotracheal tube that has been inserted into a patient. A collapsible plastic envelope surrounds the semi-rigid sheath and seals it from contamination and contact by a user. The collapsible envelope may be separated into two pieces, one connected between the manifold and the distal side of the valve, and the other connected between the proximal side of the valve and a cap at the proximal end of the apparatus. The semi-rigid sheath is resilient and provides a gripping effect acting on the slider portion of the valve to hold the valve in any position in which it may be set along the length of the sheath.

The apparatus disclosed in the aforementioned U.S. patent application has proven to be very satisfactory for many purposes and constitutes a significant improvement over the devices shown in the aforementioned U.S. patents and other similar prior art devices. Nevertheless, there remains a need for an even further improved apparatus for ventilating and aspirating the lungs of a medical patient.

SUMMARY OF THE INVENTION

The present invention provides an improved apparatus for simultaneously ventilating and aspirating a medical patient. The invention enables a user to insert a flexible catheter tube into either lung of a patient in one smooth motion without risk of contamination or infection. Additionally, a user is able to activate, in one motion, a vacuum valve to evacuate undesired respiratory fluids and simultaneously ventilate and/or irrigate the lungs.

A flexible catheter tube is attached at the proximal (user) end to a valve. The valve is selectively actuated to communicate a vacuum suction to the lumen of the catheter. The distal (patient) end of the catheter tube is structured to permit fluid to be suctioned into the lumen of the catheter tube.

The valve at the proximal end of the catheter tube is used to communicate a suctioning vacuum to the lumen of the catheter. A typical source of vacuum is the vacuum line commonly found in a hospital room. The valve contains a biasing means to urge the valve to normally closed position. A valve of the type disclosed in the parent application may be modified with additional structure to render it suitable for use with the present invention. A more preferred valve, however, while including some similar components, includes a valve structure with a side operated push button for opening the normally closed valve. No matter how the valve may be embodied, when a suctioning vacuum is desired, the user presses the valve operating means to bring the catheter into fluid flow communication with the vacuum source. The use of such a valve arrangement avoids the need for a user to involve more than one hand, either to actuate the valve or to lock it in a closed position. The user's other hand is thereby left free to aid in placement or movement of the catheter. The entire valve assembly serves as a convenient handle for inserting and withdrawing a catheter tube.

The catheter tube is slidable lengthwise through a multi-function manifold positioned at the distal end of the apparatus. The manifold may be of the type disclosed in the parent application or of any other convenient structure. Preferably, it includes several segments, including a port at the distal end for communication with an endotracheal tube inserted into the patient.

This invention is typically embodied such that a distal port is positioned at the end of a generally cylindrical passageway which extends through the length of the manifold. A proximal port is located at the opposite end of the passageway. The catheter tube is slidable through this passageway so that it enters the endotracheal tube through the distal port. A ventilating structure extends radially from the passageway and is in fluid communication with the interior of the passageway. Ambient air, oxygenated air, and other therapeutic gasses can be selectively introduced into the respiratory system of the patient through the ventilating structure. The ventilating structure may be formed so that ventilation can be accomplished by inhalation and exhalation of ventilating air through the same conduit or, in an alternate configuration, through two or more conduits, allowing inhalation of ambient air through one port and exhalation through a second port. A third conduit may also be provided for the introduction of other suitable gases to the respiratory system.

The manifold may be disposed between front (distal) and rear (proximal) swivel segments which allow the manifold to rotate in a generally coaxial manner about the catheter tube. The apparatus and any connected devices may thus be moved about independent of the endotracheal tube inserted into the patient. As a consequence, the accessibility of conduits associated with the manifold is enhanced. The attachment of tubing, such as that associated with the ventilation source, is thereby facilitated. A user may rotate the catheter as convenient to perform the aspiration function.

A sheath entirely surrounds the catheter tube when the tube is inserted into or withdrawn from the patient. The sheath is closed at its distal end and is secured with the manifold so as to become an extension of the cylindrical passageway through the manifold. The proximal end of the sheath is sealed, preferably with a rigid finger tab structure. The sheath is provided with a "self sealing" slit along one edge. While various constructions are within contemplation, a construction commonly referred to as a "zip lock" in the packaging field is presently preferred. Such a construction typically includes a pair of opposed sidewalls defining the slit and interconnectable by mutually opposed structures carried by the respective sidewalls. Typically, a bead is formed along the edge of one sidewall and a groove is formed along the edge of the other sidewall such that the bead may be pressed into a sealing engagement within the groove to provide an airtight closure of the slit.

The vacuum valve is mounted on a slider member that includes spaced-apart legs positioned to straddle the bead and groove structures carried by the edges of the respective flexible sidewalls of the sheath. The slider member is structured to move longitudinally in either direction along the sheath, interacting in either case with the sealing components of the slit. Movement of the slider continuously opens the slit in a region which is localized with respect to the slider but travels with respect to the sheath, together with the slider. Concurrently, the slider functions to reseal the slit directly behind, in the direction of travel, the moving open region. In this fashion, a substantially air tight seal is maintained across the sheath barrier.

In a typical arrangement, the legs of the slider member are configured as panels interconnected at their respective distal ends by a web. The panels converge in opposite directions from a central region at which a port is provided through the web. The port accommodates a conduit which interconnects the catheter within the sheath and an external vacuum source through a valve carried by the slider. When a "zip lock" seam construction is utilized, the slider assembly may be regarded as an air tight "zip lock" actuator.

A user, grasping the valve and/or slider member can push the valve, slider member and catheter tube in the direction of a patient, at which time the catheter tube is passed through the manifold, into, and through, an endotracheal tube in the patient. Alternatively, the valve slider member and catheter tube may be moved away from the patient, with the catheter tube always remaining sterile and protected by the sheath and manifold. The interlocking sidewall structures couple and decouple as appropriate to maintain a sealed sheath extending in both directions from the slider/valve assembly. These structures form a stiffening member that holds the sheath in a projected condition. A finger tab may optionally be provided at either or both the distal and proximal ends of the sheath to be grasped as the valve, slider member and catheter tube are reciprocated, with respect to the sheath.

A leading edge of the slider member will typically be configured to hold cooperating structures, such as a bead and groove arrangement, in an interlocked configuration. The trailing edge of the slider member will typically be configured to again interlock the cooperating structures so that the sheath is sealed during all portions of travel of the slider member, except for the portion split by a divider device associated with the slider member between its leading and trailing edges.

To maintain the sterility of the catheter tube, an airtight relationship is provided between the divider device and the cooperating structures.

In practice, various indicia may be associated with the devices of this invention to inform the user concerning the location and orientation of the distal end of the catheter tube. The longitudinal advance of the catheter may be monitored by means of indicator marks or colored segments on the catheter tube and/or barrier sheath, for example. According to certain embodiments, the slider assembly serves as a position indicator by reference to a scale imprinted on the sheath in the proximity of the self sealing slit. The radial orientation of the catheter tip is of interest for constructions utilizing a curved or bent tip. Indicia, such as index marks, associated with a swivel joint are useful for this purpose. More sophisticated embodiments carry field affecting devices, such as coils, magnets or capacitors, at the distal end of the catheter tube. The position and orientation of such devices can be precisely monitored by conventional means from outside the patient. Other embodiments monitor the catheter tip position by resort to radio opaque markers detectable by conventional radiologic techniques.

BRIEF DESCRIPTION OF THE DRAWINGS

In the drawings, which illustrate what is currently regarded as the best mode for carrying out the invention:

FIG. 1 is a perspective, partially exploded and partially broken away view of a preferred embodiment of the assembled invention;

FIG. 2 is an enlarged sectional view taken on the line 2—2 of FIG. 1;

FIG. 3 is a top plan view of a suction valve used in one embodiment of the invention;

FIG. 4 is an enlarged sectional view taken through the valve of FIG. 3;

FIG. 5 is an enlarged transverse section view taken on the line 5—5 of FIG. 4;

FIG. 6 is a transverse section through the sheath of the invention, taken on the line 6—6 of FIG. 1;

FIG. 8 is an enlarged transverse section taken on the line 8—8 through the valve of FIG. 7;

FIG. 9 is a top plan view of the valve of FIG. 7, broken away to show the structure inside;

FIG. 10 is a top plan view of the valve plunger of the valve of FIG. 7;

FIG. 11 is a side plan view of the plunger shown in FIG. 9;

FIG. 12 is a perspective view of one-half of the plunger of FIGS. 9 and 10, the other half being identical thereto;

FIG. 13 is a side elevation view, partially broken away;

DETAILED DESCRIPTION OF THE ILLUSTRATED EMBODIMENTS

Figure 16:
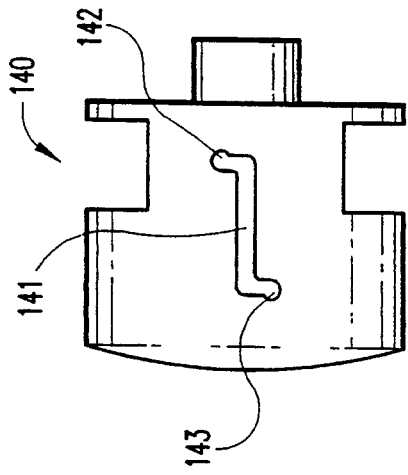
FIG. 16 is a side elevation view, like that of FIG. 11, but showing a modified plunger.

The ventilating and aspirating device, designated generally 10 in FIG. 1, includes front swivel segment 11 which attaches to an endotracheal tube associated with the patient, the endotracheal tube not being shown.

A suction catheter tube 14 includes a distal (patient) end 14A and a proximal end 14B. The distal end 14A includes radially disposed perforations 15 and an open end 16. A curved end 17 may be disposed near the distal end 14A, as shown. The proximal end 14B of the catheter tube 14 is attached to a vacuum valve shown generally at 20. During operation, the valve 20 is attached to a vacuum source (not shown) by means of a connector fitting 22. The valve 20 is actuated to apply suction to the lumen of the catheter tube 14, when desired.

When the catheter tube 14 is inserted into the endotracheal tube of the patient, the distal end 14A moves into either the endotracheal tube or a bronchus of the patient, depending on the depth of insertion. The curved end 17 is intended to facilitate entry of the catheter tube 14 into the patient's bronchi. Undesired respiratory fluids can be suctioned out of the patient's breathing passageways by actuating the valve 20. With vacuum communicated to the catheter tube 14, fluids and secretions are suctioned into the catheter tube lumen through the perforations 15 and open end 16. The fluids and secretions are then transferred out through the conduit attached to connector 22 of the valve 20.

Referring to FIG. 2, a segmented manifold assembly denoted generally at 25 includes a port casing 26, ventilation conduit 27, and ventilation port 28 disposed between the front swivel segment 11 and a rear swivel segment 29.

Port casing 26 includes a generally cylindrical passage 30 through which the catheter tube 14 moves during insertion or withdrawal. Ventilation conduit 27 extends radially from port casing 26 and is in fluid communication with the interior of the passage 30. Ambient air, oxygenated air and other therapeutic gases can be selectively introduced into the respiratory system of the patient through ventilation port 28.

The front swivel segment 11 attaches to the port casing 26 at the distal end of the passage 30. The attachment is such that the passage 30 communicates with the interior of the front swivel segment 11. The connection between the front swivel segment 11 and port casing 26 is sufficiently fluid-tight to maintain a sterile, airtight seal, but loose fitting enough to allow independent rotation of each segment. The front swivel segment 11 is adapted to attach to the patient's endotracheal tube such that the passage 30 is in fluid communication with the endotracheal tube.

The rear swivel segment 29 attaches to the port casing 26 at the proximal end of the passage 30 in a fashion generally similar to that explained in connection with front swivel segment 11. The passage 30 communicates with the interior of the rear swivel segment 29. The connection effected between the casing 26 and segment 29 also allows independent rotation of the segments as previously described.

As best seen in FIG. 2, the rear swivel segment 29 carries an "O"-ring 31 held in place by a seal cover 32. The "O"-ring 31 thus fits snugly to form a seal between the inside wall of the segment 29 and the outside wall of the "O"-ring 31. The interior surface of the "O"-ring 31 fits snugly over the catheter tube 14, forming an airtight sterility seal. The catheter tube is slidable lengthwise through the "O"-ring 31 during insertion or withdrawal of the catheter tube 14 with respect to a patient. The extended portion of the catheter tube 14 is thereby isolated from the remainder of the device 10.

Molded into the exterior wall of the rear swivel segment 29 is an irrigation conduit connector 32 which is in fluid communication with the passage 30. When an irrigating solution is injected into the conduit 33 attached to connector 32, the solution is directed onto the exterior of the catheter tube 14 and flows down the catheter tube 14 toward its distal end 14A.

The assembly of the casing segment 26, front swivel segment 11, and rear swivel segment 29 permits each of these segments to rotate coaxially around the catheter tube 14 independent of the other segments. Several significant advantages follow from this arrangement, the accessibility of ventilation conduit 27 during the attachment of the ventilation source is enhanced. The casing segment 26 and any attached hoses or tubing can also be swiveled out of the way of the user or the patient during use. The catheter tube 14 may be rotated during use to facilitate aspiration. Moreover, the irrigation extension conduit 33 can be pivoted to allowing rinsing of the complete perimeter of the catheter tube 14 during withdrawal.

A flexible sheath 34 is sealingly coupled at its distal end to a sleeve 35 of the seal cover 32 by a locking collar 36.

The sheath 34 is elongate and, as best seen in FIG. 6, includes a pair of sidewalls 37 and 38 interconnected at a bottom edge 39. Semi-rigid, but flexible backing members 40 and 41 extend respectively along upper edges of the sidewalls 37 and 38, for substantially the entire length of the sheath. A groove 42 is formed on an inside face of the backing member 40 and extends for the length of the backing member. A bead 43 is similarly formed in the backing member 41 and extends the full length of the backing member 41. The bead 43 fits tightly into the groove 42 and when the bead 43 is pressed within groove 43 for the length of the backing members 40 and 41, the sheath 34 is fully sealed.

As has been noted, the distal end of the catheter tube 14 extends through the rear swivel segment 29, the manifold assembly 25, and into and through an endotracheal tube, not shown. As shown by FIGS. 1 and 4, the proximal end of the catheter tube 14 is coupled to an elbow connector 45 at the lower end of a nipple 46 forming part of a slider assembly, shown generally at 47 (FIG. 1).

The slider assembly 47 includes a pair of legs 48 and 49, interconnected by a web 50, that straddle the backing members 40, 41 and the bead 43 and groove 42 of the sheath 34. The legs 48 and 49 and the web 50 are elongate and the legs diverge through a central portion of their length and converge at opposite ends so that as the slider assembly 47 travels along the sheath 34, the ends of the assembly force the bead 43 fully into the groove 42. The nipple 46 extends through a hole 51 formed in the web 50 and the elbow 45, at one end of the nipple 46, is connected inside the sheath 34 to the catheter tube 14. The nipple 46 and elbow connector 45 form part of an insert member 55 (FIG. 1) that also includes a series of stepped walls 56, 57 and 58. The walls 56, 57 and 58 each diverge around the nipple 46 and converge at opposite ends. A stepped surface 59 (FIGS. 1 and 5) interconnects the top of wall 56 with the bottom of the smaller wall 57 and another step surface 60 interconnects the top of wall 57 with the bottom of wall 58.

The insert member 55 extends from inside the sheath 34 into locking engagement with the slider member 47. The nipple 46 then extends through the hole 51 of the web 50 and the wall 58 serves as a divider to be positioned between corresponding portions of the bead 43 and groove 42, respectively. Thus, divider wall 58 is arranged to travel between the bead 43 and groove 42 as the slider member 47 is moved in either of its permissible directions of travel. The step surface 60 passes beneath the groove 42 during sliding movement of the slider member 47 and the wall 57 separates portions of the backing members 40 and 41 for the bead 43 and groove 42, respectively. The step 59 moves beneath the backing members 40 and 41 as the slider member is moved.

As best seen in FIG. 5, the bead 43 and groove 42, their backing members 41 and 40, and the portions of the sidewalls 37 and 38 of sheath 34 on which the backing members, bead and groove are formed, are wedged tightly between the wall 58 and the insides of walls 48 and 49 of the slider member 47 so that air cannot pass between the bead and groove, even during movement of the slider element. Similarly, the backing members 40 and 41 and sidewalls 37 and 38 are wedged between the wall 57 of the insert member and the insides of walls 48 and 49 of the slider member 47 to provide another airtight seal. Portions of the flexible sidewalls 37 and 38 of sheath 34 are also wedged between the wall 56 of the insert member 55 and the insides of legs 48 and 49 of the slider member 47. The tight, wedging relationship between the slider member 47, the insert member 55, and the components of the sheath 34 result in the insert member's being securely held within and between the legs 48 and 49 of the slider member. The tight wedging action also results in airtight seals between the bead 43 and groove 42 and wall 58 of the insert member; between the backing members 40 and 41 and wall 57 of the insert member and between a portion of the flexible sheath adjacent to the backing members and wall 56 of the insert member. Thus, an airtight seal is provided even as the slider member is moved along the sheath and the bead 43 and groove 42 are separated to allow such passage. The converging ends of the slider member provide a leading edge clamp for the bead and groove and a trailing edge clamp to close the bead and groove after the divider 58 has passed between them. A pair of stud projections 61 and 62, spaced at opposite sides of the nipple 46 project upwardly from the top surface 63 formed on the divider wall 58. The projections 61 and 62 fit into hollow well projections 64 and 65, respectively, formed on and opening through the web 50 of the slider member 47 and insure that the components of the slider member 47 and the insert member 55 move in unison.

As previously noted, the slider member 47 supports and carries a vacuum valve 20.

As best shown by FIGS. 1 and 4, the valve 20 includes a resilient cap 65 which acts as a pushbutton valve actuator and which suspends a depending valve stem 66 in a close-fit relation with a cylindrical valve body 67. When the valve 20 is assembled, a retaining ring 68 locks a skirt 69 of the cap 65 into an annular channel 70 of the valve body 67. Vacuum from a source, not shown, is applied to a connector 72 that opens into the valve body 67. The flexible stem 66 is normally biased by the resiliency of the cap 65 into an expelled position, sealing a port 73 through the connector 72. When the cap 65 is pressed in the direction indicated P, and into a flared chamber 67A formed in body 67, an internal channel 74 of the stem 66 is brought into alignment with the port 73 and the nipple 46. Vacuum is then applied to the lumen of the catheter tube 14. When pressure on the cap 65 is released, the resilience of the cap biases the stem 66 upward to the normally closed condition of the valve 20, with the stem 66 again sealing the port 73.

The valve 20, FIGS. 1 and 4, is coupled to the slider member 47 by bonding of a downwardly extending boss 75 to the nipple 46 and the inner surface of hole 51. The bottom 76 of the valve body 67 is also bonded to the top surface of the web 50 of the slider assembly 47. The valve 20 is moved with the slider member 47 along the length of sheath 34 having the bead 43 and groove 42 thereon. A user may manipulate the valve with one hand and may use the same hand to move the valve and slider along the sheath.

A protective fence 78 may be affixed to the valve body and arranged to partially surround the resilient cap 65, so as to prevent inadvertent actuation of the valve 20. A cap 79 that will just fit over the protective fence 78 is connected by a flexible tether 79A to the valve body. The cap 79, when installed over the fence 78, provides positive protection against actuation of the valve 20.

Another embodiment of vacuum valve suitable for use with the slider member 47, is shown at 80 in FIGS. 7–13. As shown, the valve 80 includes a housing 81 with a peripheral wall 82 including sidewalls 82A and 82B interconnected by end walls 82C and 82D, and having an inside configuration corresponding to the exterior configuration of the walls 48 and 49 of the slider member 47. The housing 82 includes a top cover 84 and is open at its opposite, bottom end 85 so that the lower end of the housing will telescope tightly over the walls 48 and 49 of the slider member 47. So installed, the valve 80 is locked to the slider element 47 and is movable therewith. If desired, the housing 82 of the valve may be bonded to or be formed integrally with the slider element 47.

As best shown in FIGS. 8, 9 and 13, a flexible tube 86 has one end tightly telescoped over the upwardly extending nipple 46 and has a retainer sleeve 87, FIG. 13, inserted into its other end. An elbow connector 88 has one leg 88A fixed to the top cover 84 over a hole provided through the top cover and the other leg 88B extending for connection to a source of suction, through a flexible connecting hose, (not shown). A reinforcement plate 88C (FIG. 13) may be provided between the legs 88A and 88B of the connector 88 and the top cover 84 to strengthen the connector 88 against being broken away from the valve body.

The retainer sleeve 87, FIGS. 8 and 13, includes an outwardly projecting flexible ring 89 that is inserted into the connector 88 and snaps into a groove 90. The flexible tube 86 thus extends from the nipple 46 to the bore 88D through connector 88, to which the suction source is connected.

A plunger 95 (FIGS. 9–12) extends through a hole 96 provided in the sidewall 82A of the housing 81 and serves as a pushbutton valve actuator. The plunger 95 is guided within the housing 82 by walls 97 and 98. A spring pocket 99 is fixed to a face 95C of the plunger 95 and forms a pocket for a spring 101 that acts against the interior of the wall 82B and tends to bias the plunger out of the housing 81. The plunger 95 is preferably formed from identical halves 95A and 95B, each including one-half of the spring pocket and a pair of partial slots 100 formed in the side wall thereof at opposite sides of a generally half-barrel shaped plunger part. Alternatively, the plunger 95 can be formed in a generally cylindrical shape with the face 95C and spring pocket 99 being formed as one part and fixed to the plunger 95. When the plunger part is assembled, the plunger is of generally barrel configuration and the spring pocket is generally cylindrical. The assembled plunger then has aligned slots 100 through its top and bottom surfaces. The flexible tube 86 extends through the top and bottom slots 100 and holds the plunger in place, within the housing 82. Spring 101, in acting to bias the plunger 95 from the housing 82, causes the inside wall of the plunger to compress the flexible tubing 86 and to thereby prevent flow through the tubing. When the plunger 95 is pushed inwardly by a user, the pressure on the tube 86 is relieved and the natural resilience of the tube 86 opens the tube to permit flow therethrough.

"L"-shaped locking grooves 102 and 102A (FIGS. 11–12) may be provided in opposite sides of the wall of plunger 95 and between the grooves 101. Corresponding lug members 103 and 103A, FIG. 9, may be provided in the housing 82 such that the lug members will extend into grooves 102 and 102A. Axial rotation of the inwardly pushed plunger 95 and slots 102 and 102A will position the lugs 103 and 103A in the corresponding angled legs of the locking grooves so that spring 101 is no longer able to bias the plunger and to close the valve. In this position, the valve 80 is locked open, and pressure on the flexible tube 86 is relieved. To again close the valve, it is only necessary for the user to axially rotate the plunger 95 in the opposite direction until the locking lugs are moved away from the angled legs of the grooves 102 and 102A. The spring 101 is then free again to bias the plunger outwardly and to compress the tube 86. Similarly, when plunger 95 is fully biased by spring 101 and the tube 86 is compressed, axial rotation of the plunger will position lugs 105 and 105A in corresponding "L"-shaped grooves 104 and 104A in the plunger 95 such that the plunger cannot be pushed inwardly without first axially rotating the plunger in the opposite direction until the legs 105 and 105A are moved out of registration with the angled legs of the grooves. Tubing life is extended if the plunger is locked in the valve open position during periods of non-valve use, for example, during sterilization, storage and shipping.

As with the previously disclosed valve 20, the valve 80 can be operated with one hand of a user and will slide with the slider element 87 along the length of sheath 34. The bead and groove configuration, together with the backing members provided by the sheath 34 provide sufficient rigidity to maintain the sheath in a substantially extended position. However, some flexibility is retained to allow a user to reposition the sheath as necessary, relative to other equipment being used during an operation. Finger tabs (or pads) 106 and 106A at the proximal and distal ends of the sheath allow the user to anchor the sheath while running the slider member and valve along the sheath. Either or both tabs 106, 106A may be color coded or otherwise marked to indicate to an operator the intended function of the respective tabs. The proximal tab 106 functions as an anchor for the pliant sheath 34 during extension of the catheter 14 into the trachea of a patient. The distal tab 106A anchors the sheath 34 when the catheter 14 is withdrawn from the patient.

Another embodiment of manifold assembly, shown generally at 10 (FIG. 14) corresponds to and may be used in place of the manifold assembly 25, previously described. As with the previously described structure, a front swivel segment 111 that attaches to an endotracheal tube, not shown, but inserted into a patient, has the manifold assembly secured thereto.

Figure 14:
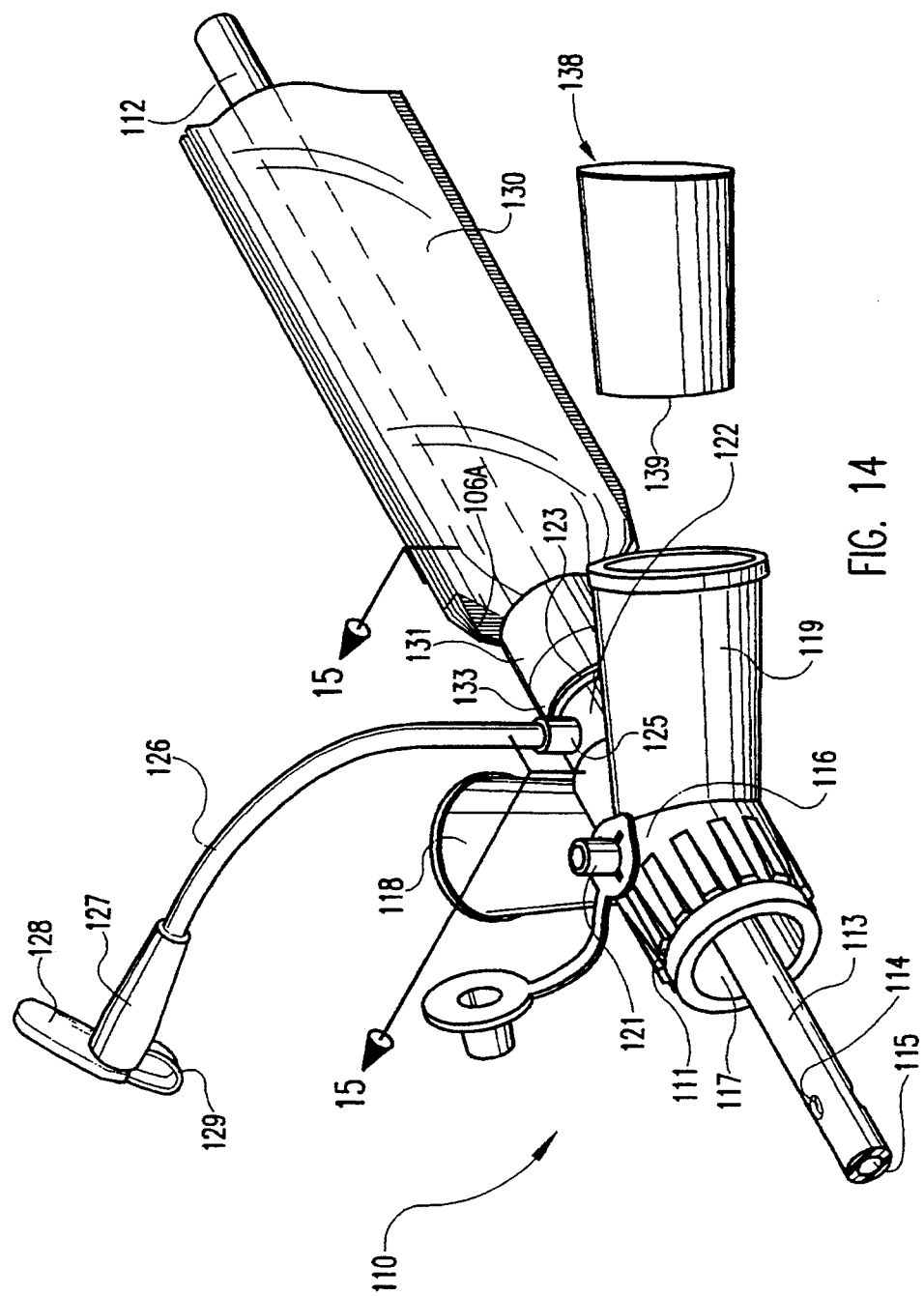
FIG. 14 is a perspective view of another embodiment of manifold of the invention.

In the embodiment shown in FIG. 14, a suction catheter tube 112 has a straight distal end 113 and a proximal end (not shown in FIG. 14). The end 113 projects from the swivel segment 111 and has side perforations 114 and an end opening 115.

The manifold assembly 110 includes a body 116 with a passage 117 therethrough, through which the tube 112 is passed. The body 116 attaches to the front swivel segment 111 such that the passage 117 communicates with the interior of the swivel segment 111 and the connection allows independent rotation between the swivel segment 111 and the body 116.

Figure 15:
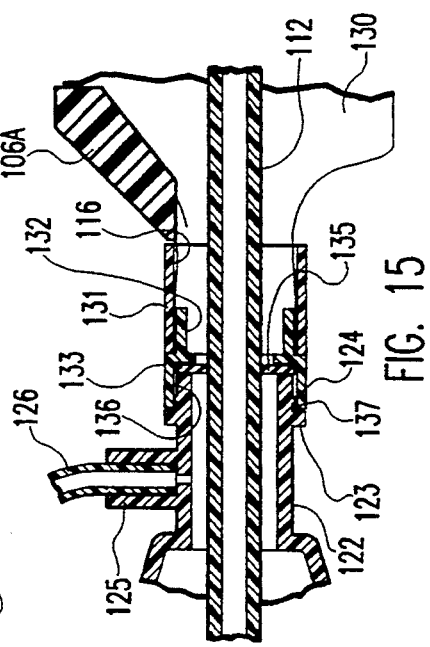
FIG. 15 is a fragmentary section view taken on the line 15—15 of FIG. 14.
Figure 7:
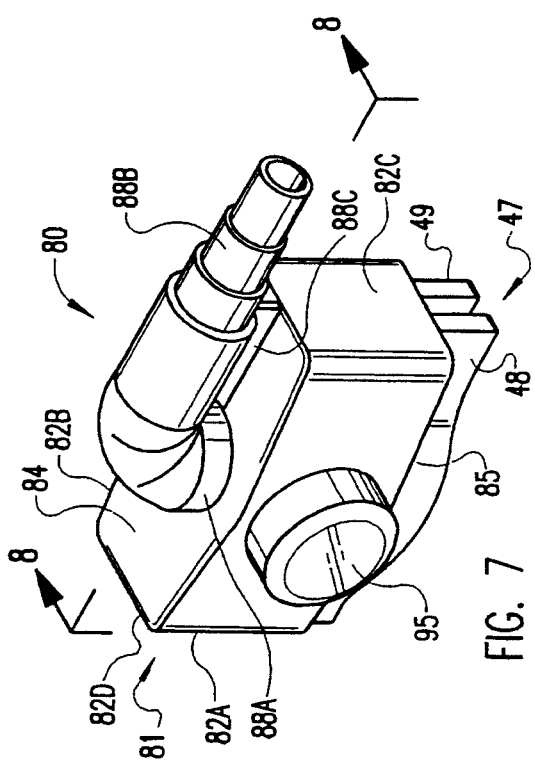
FIG. 7 is a perspective view of another embodiment of suction valve suitable for use with the invention.

The body 116 has a pair of angled connector members 118 and 119, each opening into the passage 117, a pressure sensor connector 121, and a sheath connector 122, each extending from the body and each opening into the passage 117. The sheath connector 122 includes a collar 123, FIG. 15, and a plurality of partially encircling edges 124. An irrigation conduit connector 125 projects from the sheath connector 122 and opens into the sheath connector 122 to be in communication with passage 117. A flexible irrigation conduit 126 has one end connected into the irrigation conduit connector 125 and has one end of a tubular connector member 127 on the free end thereof. A cap 128 is formed to fit over the other end of tubular connector member 127 and flexible tether 129 interconnects the connector member 127 and the cap 128 which removably fits into and tightly closes the connector member.

The sheath 130 is constructed in the same manner as the sheath 34 previously described and has a sleeve 131 secured to the open end thereof. The sleeve 131, with the attached end of sheath 130, is telescoped onto a step-down shoulder 132 of a plug 133 having a central hole therethrough, through which the suction catheter tube 112 is passed. A seal 135, FIG. 15, fits within a bore 136 of the plug 133 and snugly around the catheter tube 112 as the tube is passed therethrough. The bore 136 telescopes over the sheath connector 122 and a small ridge 137 on the inside outer edge of the bore snaps over the partially encircling ridges 124 to hold the plug 133, sleeve 131 and sheath 130 securely to the manifold assembly 110, with the airtight seal between the plug 133 and end of the sheath connector 122.

The manifold assembly 110, when attached to the sheath 130, functions with respect to the catheter tube 112 and sheath 130 in generally the same manner as the manifold assembly 25 functions with respect to the sheath 34 and its attached structures. One or both connector members 118 and 119 can be used for the selective introduction of ambient air, oxygenated air and other therapeutic gases to the patient. The pressure sensor connector 121 provides a means for attachment of a sensing device, not shown, for use in determining the pressure in a patient's chest. The irrigation conduit connector 125 permits the introduction of fluids to cleanse the catheter tube as it is withdrawn from a patient, in the manner previously described.

As illustrated by FIG. 14, a separate connector member plug, designated generally 138, may be provided to fill the interior space of either or both of the members 118, 119. The plug 138, as shown, is configured to eliminate dead air space in a member, 118, 119, not in use and is configured at its distal end 139 to merge with the interior side wall defining passage 117.

Another embodiment of plunger is shown at 140 in FIG. 16. The plunger 120 differs from the plunger 95, as shown in FIG. 11, only in that it includes a single slot 141 having a first "L"-shaped end 142 and a second "L"-shaped end 143, rather than the plural slots 102 and 104 shown in FIG. 11. Only a single lug member, i.e. member 103, is required to extend into slot 141. Thus, when the plunger is fully expelled, the plunger 140 may be turned to position lug 103 in the "L"-shaped end 142 and to thereby prevent inadvertent pushing of the plunger and opening of flow through the tube 86. Similarly, when the plunger is pushed to allow flow through tube 86, the plunger may be turned to position lug member 103 in the "L"-shaped end 143. The plunger is thereby held in its pushed-in position, insuring continuous access of sterilization gases through the tube 86.

While a locked open position is generally inappropriate for therapeutic applications, it is useful for sterilization, storage and shipping. The open condition relieves mechanical pressure and crimping stress on the tube 86 prior to its actual use.

While this disclosure has placed principal emphasis on tracheal aspirating devices, the invention is broadly applicable to other circumstances in which it is desired to manipulate an instrument across a barrier, particularly a sanitary barrier. Various medical applications involving catheter placement or other intubation procedures are within contemplation. Other, more elaborate embodiments may utilize the air tight ziplock slider construction of this invention to facilitate movement of probes or other devices to various locations about a surface defining an enclosed space. A typical such embodiment involves the positioning of one or more flexible gloves with respect to another such glove or device to facilitate the examination or manipulation of objects within an enclosed space from outside that space.

The invention may be viewed broadly as a protective shield apparatus which permits the manipulation or positioning of an implement on one side of a barrier, typically within a confined or protected space, by manual or mechanical motion induced from the opposite side of the barrier by means of an actuator assembly. The actuator assembly is dynamically locatable at substantially any point along a travel path defined by a releasably closed parting line or slit opening through the barrier. The barrier is typically pliant to accommodate sealable parting constructions of the ziplock type or their mechanical equivalents. The barrier may be configured as a sheath, as illustrated, but it may alternatively be structured as a rigid or semirigid dome or other housing characterized by a surface capable of maintaining parting line adaptable to actuator travel.

References herein to the details of the illustrated embodiments are by way of example only and are not intended to limit the scope of the appended claims which themselves recite those features regarded as important to the invention.

What is claimed is:

1. A protective shield apparatus for allowing communication between a user located on a first side of a barrier and an implement for use with said protective shield, said implement located on a second side of said barrier across at least one channel dynamically locatable anywhere along a defined course of potential channel location through said barrier, said protective shield apparatus comprising:

anchoring means for allowing insertion of a portion of said implement therethrough;

a pliant barrier means defining a substantially discrete space;

at least one releasably sealable slit formed through said barrier means, said slit defining a course of travel along said barrier means, said slit having one portion thereof releasably connected to another portion thereof thereby providing physical sealing of said slit to prevent substantial airflow through said slit; and connector means for allowing communication across said at least one channel between a user and said implement for use with said protective shield apparatus, said connector means including structure disposed through said at least one slit and being otherwise structured and arranged for slidable movement along said course, whereby to open a portion of said slit adjacent said connector means progressively in the direction of movement of said connector means while concurrently closing said slit following said connector means in the direction of movement.

2. The protective shield apparatus of claim 1 further including:

vacuum pressure source positioned for access by a user;

wherein said implement comprises a flexible catheter tube being extendable into and withdrawable from the trachea of a patient, said catheter tube having a longitudinal catheter axis, a catheter lumen and a distal end structured to permit secretions from a patient to enter said catheter lumen;

wherein said pliant barrier means comprises a pliant sheath formed of a substantially continuous sidewall and having a longitudinal sheath axis, said pliant sheath receiving and coaxially surrounding said catheter tube, said pliant sheath having a closed proximal end and an open distal end through which said catheter tube is slidable;

said connector means comprises a vacuum valve having an inlet connected to the lumen of said catheter tube, an outlet constituting means for connection to said vacuum pressure source, and a valve actuator for selectively communicating the lumen of said catheter tube with said vacuum pressure source; and wherein said anchoring means comprises a manifold connected to the distal end of said pliant sheath and having a center passage in open communication with the interior of said pliant sheath, said manifold including a first end, a second end, and opening means for establishing a fluid connection between said center passage and a patient ventilation and exhalation apparatus and being structured to permit slidable passage of said catheter tube through said center passage.

3. The protective shield apparatus of claim 2 wherein the manifold includes first port means for selectively introducing a lavage solution into the center passage to irrigate the exterior and interior of said catheter tube during and following retraction of the catheter tube into said pliant sheath.

4. The protective shield apparatus of claim 2 wherein the manifold includes a first swivel structure axially rotatably mounted to the first end of said manifold, the first swivel structure having an interior in open communication with said center passage and an "O"-ring seal structure disposed so as to be capable of substantially sealing the interior of said sheath from the center passage and wiping the exterior of said catheter tube during retraction of the catheter tube into the sheath.

5. The protective shield apparatus of claim 4 wherein the manifold further includes a second swivel structure axially rotatably mounted to the second end of said manifold opposite the first end on which the first swivel structure is mounted, the second swivel structure having an interior in open communication with said center passage.

6. The protective shield apparatus of claim 4 wherein said distal end of said flexible catheter tube includes at least one radially disposed perforation which in conjunction with negative pressure therethrough from said vacuum pressure source facilitates the breaking up of human secretions and other liquids of relatively high viscosity in the course of evacuation of said secretions and liquids.

7. The protective shield apparatus of claim 2 wherein at least one of said pliant sheath and catheter carries externally visually perceived longitudinal indicia denoting the extent of advancement of said catheter tube into the trachea of a patient.

8. The protective shield apparatus of claim 4 wherein at least one of said first swivel structure and catheter carries externally visually perceived indicia denoting the radial positioning of said catheter tube.

9. The protective shield apparatus of claim 2 wherein said pliant sheath comprises a first pad positioned at the proximal end whereby the pliant sheath may be anchored as said catheter tube is advanced into the trachea of a patient and whereby the direction of said catheter tube being extendable into and withdrawable from the trachea of a patient may be influenced.

10. The protective shield apparatus of claim 9 wherein said pliant sheath further comprises a second pad positioned at the distal end whereby the pliant sheath may be anchored as said catheter tube is retracted from the trachea of a patient.

11. The protective shield apparatus of claim 10 wherein said first pad includes a visually perceived first indicator of the function of the first pad and wherein said second pad includes a visually perceived second indicator of the function of the second pad.

12. The protective shield apparatus of claim 10 wherein said first indicator is color coding with relief and print inscriptions and wherein said second indicator is color coding with relief and print inscriptions.

13. The protective shield apparatus of claim 2 wherein said manifold includes second port means for monitoring conditions within said center passages.

14. The protective shield apparatus of claim 2 wherein said opening means of said manifold comprises a first conduit structure configured to allow relatively low dead air space therein, extending radially from said manifold and in communication with said center passage for selective communication of ventilating gases between a therapeutic ventilator and a patient.

15. The protective shield apparatus of claim 14 wherein said opening means further comprises a second conduit structure configured to allow relatively low dead air space therein, extending radially from said manifold and in fluid communication with said center passage for selective communication of ventilating gases between a therapeutic ventilator and a patient.

16. The protective shield apparatus of claim 15 wherein a plug for use in said first or second conduit structure is placed within said first or second conduit structure whereby fluid communication with said center passage through said conduit structure is prevented and dead air space in said first or second conduit structure is substantially avoided.

17. The protective shield apparatus of claim 2 wherein said pliant sheath provides a sterility preserving casing about said catheter tube and a limitation to migration of contaminants from a patient through said sheath to a user.

18. The protective shield apparatus of claim 1 wherein said communication between a user and an implement includes direct physical contact.

19. The protective shield apparatus of claim 18 wherein said communication between a user and an implement includes fluid communication.

20. The protective shield of claim 1 including closing means for releasably closing said slit along its entire length, said closing means comprising a bead formed along a first edge of said slit and a groove formed along a second edge of said slit to tightly receive said bead, thereby to prevent air flow through said slit.

21. A protective shield apparatus for allowing communication between a user located on a first side of a barrier and a catheter tube for use with said protective shield apparatus, said catheter tube located on a second side of said barrier across at least one channel dynamically locatable anywhere along a defined course of potential channel location through said barrier, comprising:
a pliant barrier means defining a substantially discrete space;
at least one releasably closed slit formed through said barrier means, said slit defining a course of travel along said barrier means;
connector means for allowing communication across said at least one channel between a user and said catheter tube for use with said protective shield apparatus, said connector means including structure disposed through said at least one slit and being otherwise structured and arranged for slidable movement along said course, whereby to open a portion of said slit adjacent said connector means progressively in the direction of movement of said connector means while concurrently closing said slit following said connector means in the direction of movement; and
closing means for releasably closing said slit along its entire length, said closing means comprising a backing member formed along each said edge of said slit, a bead formed along a first edge of said backing member and a groove formed along a second edge of said backing member to tightly receive said bead, thereby to prevent air flow through said slit.

22. The protective shield of claim 21 wherein the connector means includes a slider member having legs straddling a portion of said means for releasably closing said slot and a web interconnecting said legs, and said legs and web converging at opposite ends thereof, whereby the ends of said legs hold the slot closed and diverge at a central portion thereof; a divider member between the legs at a central portion thereof and shaped to open the slot at said central portion; and a conduit means extending through said divider means for releasably closing said slot and having one end connected to the catheter tube inside the sheath and its other end projecting through the web of the slider member to be connected to a suction source.

23. The protective shield of claim 22 wherein the divider member is a portion of an insert member, inserted into the slider member from within the sheath and further including stepped walls for engaging the backing members and the sheath material of the sheath when said insert member is wedged into the slider member, between the spaced legs.

24. The protective shield of claim 23 wherein the vacuum valve is carried by the slider member and includes a valve body secured to the slider member and a passageway in said valve body connected to the catheter tube; and further including:
a conduit connector opening into said passageway;
a valve actuator to open the valve;
means biasing the valve actuator to a valve-closed position;
means preventing flow from the catheter tube to the conduit connector when the valve is in a valve-closed position; and
means connecting the catheter tube to the conduit connector for flow therebetween upon movement of said valve actuator to a valve-open position.

25. A protective shield as in claim 24, wherein:
the valve actuator includes a valve stem extending therefrom into the valve body, said valve stem having a passage therethrough for flow from the catheter tube to the conduit connector; and
the means biasing the valve actuator comprises a resilient pushbutton portion of the valve actuator.

26. The protective shield of claim 25, wherein the valve actuator includes a flexible tube extending through the valve body, and wherein the means biasing the valve actuator biases the valve actuator to compress the flexible tubing to prevent flow therethrough.

27. The protective shield of claim 26, wherein:
the valve actuator compresses a plunger slidable into a sidewall of the valve body and said plunger having a hole therethrough inside the valve body;
the biasing means compresses a spring positioned between an opposite sidewall of the valve body and the plunger; and
the flexible tubing extends through the hole in the plunger to secure the plunger in the valve body.

28. The protective shield of claim 27, further including means to lock the plunger in a valve-open position.

29. The protective shield of claim 28, further including means to lock the plunger in a valve-closed position.

30. A protective shield apparatus for allowing communication between a user located on a first side of a barrier an catheter tube for use with said protective shield apparatus, said catheter tube located on a second side of said barrier across at least one channel dynamically locatable anywhere along a defined course of potential channel location through said barrier, comprising:
a pliant barrier means defining a substantially discrete space;
at least one releasably closed slit formed through said barrier means, said slit defining a course of travel along said barrier means;
closing means for releasably closing said slit along its entire length, said closing means comprising a bead formed along a first edge of said slit and a groove formed along a second edge of said slit to tightly receive said bead, thereby to prevent air flow through said slit; and
connector means for allowing communication across said at least one channel between a user and said catheter tube for use with said protective shield apparatus, said connector means including structure disposed through said at least one slit and being otherwise structured and arranged for slidable movement along said course, whereby to open a portion of said slit adjacent said connector means progressively in the direction of movement of said connector means while concurrently closing said slit following said connector means in the direction of movement, the connector means including a slider member having legs straddling a portion of said closing means and a web interconnecting said legs, said legs converging at their respective opposite ends, whereby ,said ends function to hold the bead in the groove, and said legs diverging at a central portion of said slider member; a divider member between said legs at said central portion and shaped to separate the bead from the groove at said central portion; and a conduit means extending through said divider member and having a first end connected to the catheter tube inside the sheath and a second end projecting through the web of the slider member.

31. The protective shield of claim 30 wherein the divider member is a portion of an insert member, inserted into the slider member from within the sheath and further including stepped walls for engaging the material of the sheath when said insert member is wedged into the slider member, between the spaced legs.

32. The protective shield of claim 31 wherein the vacuum valve is carried by the slider member and includes a valve body secured to the slider member and a passageway in said valve body connected to the catheter tube; and further including:
a conduit connector opening into said passageway;
a valve actuator to open the valve;
means biasing the valve actuator to a valve-closed position;
means preventing flow from the catheter tube to the conduit connector when the valve is in a valve-closed position; and
means connecting the catheter tube to the conduit connector for flow therebetween upon movement of said valve actuator to a valve-open position.

33. The protective shield of claim 24, wherein:
the valve actuator includes a valve stem extending therefrom into the valve body, said valve stem having a passage therethrough for flow from the catheter tube to the conduit connector; and
the means biasing the valve actuator comprises a resilient pushbutton portion of the valve actuator.

34. The protective shield of claim 25, wherein the valve actuator includes a flexible tube extending through the valve body, and wherein the means biasing the valve actuator biases the valve actuator to compress the flexible tubing to prevent flow therethrough.

35. The protective shield of claim 34, wherein:
the valve actuator compresses a plunger slidable into a sidewall of the valve body and said plunger having a hole therethrough inside the valve body;
the biasing means compresses a spring positioned between an opposite sidewall of the valve body and the plunger; and
the flexible tubing extends through the hole in the plunger to secure the plunger in the valve body.

36. The protective shield of claim 35, further including means to lock the plunger in a valve-open position.

37. The protective shield of claim 36, further including means to lock the plunger in a valve-closed position.

38. The protective shield apparatus of claim 1, wherein said protective shield apparatus comprises an improved ventilating and aspirating apparatus for delivering respiratory gases to the trachea of a patient and aspirating congested lugs and breathing passageways of a patient, said ventilating and aspirating apparatus further comprising:
said implement comprising a flexible catheter tube having a catheter lumen and a longitudinal catheter axis, said catheter tube being extendable into and withdrawable from a patient's trachea and having a distal end structured to permit secretions to enter said catheter lumen;
a vacuum valve with an inlet connected to the lumen of said catheter tube, an outlet constituting means for connection to a vacuum source, and an actuator for selectively communicating the lumen of said catheter tube with the vacuum source;
said pliant barrier means comprising a pliant sheath formed of a substantially continuous sidewall and having a longitudinal sheath axis, said sheath receiving and coaxially surrounding said catheter tube, having an open distal end through which said catheter tube is slidable and a releasably closed slit formed in a portion of said sidewall, said slit being defined by opposed edges of a discontinuous portion of said sidewall;
a manifold connected to the distal end of said sheath having a center passage in open communication with the interior of said sheath, said manifold including means for establishing a fluid connection between said center passage and a patient ventilation and exhalation apparatus and being structured to permit slidable passage of said catheter tube through said center passage; and
said connector means for connecting said catheter tube inside the sheath to the vacuum valve outside the sheath, said connector means including structure disposed through said slit and being otherwise structured and arranged for movement parallel said sheath axis, whereby to open a portion of said slit adjacent said connector means progressively in a direction of travel of said connector means while concurrently closing said slit following said connector means in said direction of travel.

39. The improved ventilating and aspirating apparatus of claim 38 including closing means for releasably closing said slit along its entire length, said closing means comprising a bead formed along a first edge of said slit and a groove formed along a second edge of said slit to tightly receive said bead, thereby to prevent air flow through said slit.

40. An improved ventilating and aspirating apparatus as in claim 39 wherein the connector means includes a slider member having legs straddling a portion of said closing means and a web interconnecting said legs, said legs converging at their respective opposite ends, whereby said ends function to hold the bead in the groove, and said legs diverging at a central portion of said slider member; a divider member between said legs at said central portion and shaped to separate the bead from the groove at said central portion; and a conduit means extending through said divider member and having a first end connected to the catheter tube inside the sheath and a second end projecting through the web of the slider member.

41. An improved ventilating and aspirating apparatus as in claim 40 wherein the divider member is a portion of an insert member, inserted into the slider member from within the sheath and further including stepped walls for engaging the material of the sheath when said insert member is wedged into the slider member, between the spaced legs.

42. An improved ventilating and aspirating apparatus as in claim 41 for delivering respiratory gases to the trachea of a patient and aspirating congested lungs and breathing passageways wherein the vacuum valve is carried by the slider member and includes a valve body secured to the slider member and a passageway in said valve body connected to the catheter tube; and further including:
   a conduit connector opening into said passageway;
   a valve actuator to open the valve:
   means biasing the valve actuator to a valve-closed position;
   means preventing flow from the catheter tube to the conduit connector when the valve is in a valve-closed position; and
   means connecting the catheter tube to the conduit connector for flow therebetween upon movement of said valve actuator to a valve-open position.

43. An improved ventilating and aspirating apparatus as in claim 42 for delivering respiratory gases to the trachea of a patient and aspirating congested lungs and breathing passageways, wherein:
   the valve actuator includes a valve stem extending therefrom into the valve body, said valve stem having a passage therethrough for flow from the catheter tube to the conduit connector; and
   the means biasing the valve actuator comprises a resilient pushbutton portion of the valve actuator.

44. An improved ventilating said aspirating apparatus as in claim 43, for delivering respiratory gases to the trachea of a patient, and aspirating congested lungs and breathing passageways, wherein the valve actuator includes a flexible tube extending through the valve body, and wherein the means biasing the valve actuator biases the valve actuator to compress the flexible tubing to prevent flow therethrough.

45. An improved ventilating and aspirating apparatus as in claim 44, for delivering respiratory gases to the trachea of a patient and aspirating congested lungs and breathing passageways, wherein:
   the valve actuator compresses a plunger slidable into a sidewall of the valve body and said plunger having a hole therethrough inside the valve body;
   the biasing means compresses a spring positioned between an opposite sidewall of the valve body and the plunger; and
   the flexible tubing extends through the hole in the plunger to secure the plunger in the valve body.

46. An improved ventilating and aspirating apparatus as in claim 45, for delivering respiratory gases to the trachea of a patient and aspirating congested passageways, further including means to lock the plunger in a valve-open position.

47. An improved ventilating and aspirating apparatus as in claim 46 including means to lock the plunger in a valve-closed position.

48. The improved ventilating and aspirating apparatus of claim 38 including closing means for releasably closing said slit along its entire length, said closing means comprising a backing member formed along each said edge of said slit, a bead formed along a first said backing member and a groove formed along a second said backing member to tightly receive said bead, thereby to prevent air flow through said slit.

49. An improved ventilating and aspirating apparatus as in claim 48 wherein the connector means includes a slider member having legs straddling a portion of said means for releasably closing said slit and a web interconnecting said legs, and said legs and web converging at opposite ends thereof, whereby the ends of said legs hold said slit closed and diverge at a central portion thereof; a divider member between the legs at a central portion thereof and shaped to open the slit at said central portion; and a conduit means extending through said divider means for releasably closing said slit and having one end connected to the catheter tube inside the sheath and its other end projecting through the web of the slider member to be connected to a suction source.

50. An improved ventilating and aspirating apparatus as in claim 49 wherein the divider member is a portion of an insert member, inserted into the slider member from within the sheath said further including stepped walls for engaging the backing members and the sheath material of the sheath whets said insert member is wedged into the slider member, between the spaced legs.

51. An improved ventilating and aspirating apparatus as in claim 50 for delivering respiratory gases to the trachea of a patient and aspirating congested lungs and breathing passageways wherein the vacuum valve is carried by the slider member and includes a valve body secured to the slider member and a passageway in said valve body connected to the catheter tube; and further including:
   a conduit connector opening into said passageway;
   a valve actuator to open the valve;
   means biasing the valve actuator to a valve-closed position;
   means preventing flow from the catheter tube to the conduit connector when the valve is in a valve-closed position; and
   means connecting the catheter tribe to the conduit connector for flow therebetween upon movement of said valve actuator to a valve-open position.

52. An improved ventilating and aspirating apparatus for delivering respiratory gases to the trachea of a patient and aspirating congested lungs and breathing passageways as in claim 51, wherein:
   the valve actuator includes a valve stem extending therefrom into the valve body, said valve stem having a passage therethrough for flow from the catheter tube to the conduit connector; and
   the means biasing the valve actuator comprises a resilient pushbutton portion of the valve actuator.

53. An improved ventilating and aspirating apparatus in claim 52, for delivering respiratory gases to the trachea of a patient, and aspirating congested lungs and breathing passageways as, wherein the valve actuator includes a flexible tube extending through the valve body, and wherein the means biasing the valve actuator biases the valve actuator to compress the flexible tubing to prevent flow therethrough.

54. An improved ventilating and aspirating apparatus as in claim 53, for delivering respiratory gases to the trachea of a patient and aspirating congested lungs and breathing passageways, wherein:
   the valve actuator compresses a plunger slidable into a sidewall of the valve body and said plunger having a hole therethrough inside the valve body;

the biasing means compresses a spring positioned between an opposite sidewall of the valve body and the plunger; and the flexible tubing extends through the hole in the plunger to secure the plunger in the valve body.

55. An improved ventilating and aspirating apparatus as in claim 54, for delivering respiratory gases to the trachea of a patient and aspirating congested passageways, further including means to lock the plunger in a valve-open position.

56. An improved ventilating and aspirating apparatus as in claim 55 including means to lock the plunger in a valve-closed position.

57. An improved ventilating and aspirating apparatus as in claim 49 wherein the manifold includes a first swivel structure axially rotatably mounted to one end of said manifold, the first swivel structure having an interior in open communication with said center passage and an "O"-ring seal structure disposed so as to be capable of substantially sealing the interior of said sheath from the center passage and wiping the exterior of said catheter tube during retraction of the catheter tube into the sheath.

58. An improved ventilating and aspirating apparatus as in claim 57 wherein the manifold further includes a second swivel structure axially rotatably mounted to the end of said manifold opposite the end on which the first swivel structure is mounted, the second swivel structure having an interior in open communication with said center passage.

59. An improved ventilating and aspirating apparatus as in claim 57 wherein said distal end of said flexible catheter tube includes at least one radially disposed perforation which in conjunction with negative pressure therethrough from said vacuum pressure source facilitates the breaking up of human secretions and other liquids of relatively high viscosity in the course of evacuation of said secretions and liquids.

60. An improved ventilating and aspirating apparatus as in claim 57 wherein said first swivel structure comprises externally visually perceived indicia denoting the radial positioning of said catheter tube.

61. An improved ventilating and aspirating apparatus as in claim 49 wherein said manifold comprises a first conduit structure extending radially from the manifold and in fluid communication with said center passage for selective communication of ventilating gases between a therapeutic ventilator and a patient.

62. An improved ventilating and aspirating apparatus as in claim 61 wherein said manifold further comprises a second conduit structure extending radially from said manifold and in fluid communication with said center passage for selective communication of ventilating gases between a therapeutic ventilator and a patient.

63. An improved ventilating and aspirating apparatus as in claim 62 wherein selectively either and both of said conduit structure has placed therein a plug for use in said first or second conduit structure whereby fluid communication with said center passage is prevented and dead air space in said first or second conduit structure is substantially voided.

64. An improved ventilating and aspirating apparatus as in claim 49 wherein the manifold includes first port means for selectively introducing a lavage solution in into the center passage to irrigate the exterior and integer of said catheter tube during and following retraction of the catheter robe into said pliant sheath.

65. An improved ventilating and aspirating apparatus as in claim 49 wherein said manifold includes second port means for monitoring conditions within said center passage, said conditions selectively including at least gas type, gas flow rate, pressure, temperature, humidity level and liquid type.

66. An improved ventilating and aspirating apparatus as in claim 49 wherein said pliant sheath provides a sterility preserving casing about said catheter tube and a limitation to migration of contaminants from a patient through said sheath to a user.

67. An improved ventilating and aspirating apparatus as in claim 49 wherein said pliant sheath comprises a first pad positioned at the proximal end whereby the pliant sheath may be anchored as said catheter tube is advanced into the trachea of a patient and whereby the direction of extension of said catheter tube into the trachea of a patient may be influenced.

68. An improved ventilating and aspirating apparatus as in claim 67 wherein said pliant sheath further comprises a second pad positioned at the distal end whereby the pliant sheath may be anchored as said catheter tube is retracted from the trachea of a patient.

69. An improved ventilating and aspirating apparatus as in claim 69 wherein said first pad includes a visually perceived first indicator of the function of the first pad and wherein said second pad includes a visually perceived second indicator of the function of the second pad.

70. An improved ventilating and aspirating apparatus as in claim 69 wherein said first indicator is color coding with relief and print inscriptions and wherein said second indicator is color coding with relief and print inscriptions.

* * * * *